United States Patent
àWengen

[19]

[11] Patent Number: 6,099,462
[45] Date of Patent: Aug. 8, 2000

[54] IMPLANTABLE HEARING AID AND METHOD FOR IMPLANTING THE SAME

[76] Inventor: Daniel F. àWengen, Hölzliweg 9, CH-4106 Therwil, Switzerland

[21] Appl. No.: 09/250,740

[22] Filed: Feb. 16, 1999

[30] Foreign Application Priority Data

Feb. 16, 1999 [EP] European Pat. Off. .............. 98102624

[51] Int. Cl.⁷ .................................................. H04R 25/00
[52] U.S. Cl. ............................................................ 600/25
[58] Field of Search .......................... 600/25; 607/55–57

[56] References Cited

U.S. PATENT DOCUMENTS

| | | |
|---|---|---|
| 3,712,962 | 1/1973 | Epley . |
| 4,596,902 | 6/1986 | Gilman . |
| 4,601,723 | 7/1986 | McGrew . |
| 5,015,224 | 5/1991 | Maniglia . |
| 5,176,620 | 1/1993 | Gilman . |
| 5,318,502 | 6/1994 | Gilman . |
| 5,411,467 | 5/1995 | Hortmann . |
| 5,430,801 | 7/1995 | Hill . |
| 5,554,096 | 9/1996 | Ball ............................................ 600/25 |
| 5,558,618 | 9/1996 | Maniglia . |

FOREIGN PATENT DOCUMENTS 9730565 8/1997 WIPO .

*Primary Examiner*—Max Hindenburg
*Assistant Examiner*—Ryan Carter
*Attorney, Agent, or Firm*—Ostrolenk, Faber, Gerb & Soffen, LLP

[57] ABSTRACT

The hearing aid comprises a external microphone, amplifier and battery assembly transmitting its signals to a transducer structure arranged on the squama temporalis. A transducer in the transducer structure generates oscillating motions that are transferred to a vibration transmitter arranged in a groove extending along the bony external auditory canal wall. A clip at the distal end of the vibration transmitter is coupled to the long process of the incus. The hearing aid is easy to implant and provides efficient coupling of the mechanical oscillations to the ossicles of the middle ear.

16 Claims, 2 Drawing Sheets

IMPLANTABLE HEARING AID AND METHOD FOR IMPLANTING THE SAME

CROSS REFERENCE TO RELATED APPLICATIONS

This application claims the priority of European application 98102624.8, filed Feb. 16, 1998, the disclosure of which is incorporated herein by reference in its entirety.

BACKGROUND OF THE INVENTION

The invention relates to an implantable hearing aid for mechanically actuating an ossicle of the middle ear as well as to a method for implanting the same.

Various implantable hearing aids acting on an ossicle of the middle ear have been proposed. Such devices are either based on magnetic or mechanical coupling for generating vibrations of the ossicle. If mechanical coupling is to be used, complex mastoid surgery is required in order to drill a hole into the temporal bone for receiving the coupling means between an outer part of the implant and the middle ear ossicles.

U.S. Pat. No. 5,176,620 describes a hearing aid comprising a fluid mechanical coupler extending through a hole in the temporal bone and connected directly to the cochlea. Such a device is, however, difficult to implant as it requires to drill an accurate and thin hole through the cranium.

BRIEF SUMMARY OF THE INVENTION

Hence, it is a general object of the invention to provide an implantable hearing aid or implantation technique that require no complex surgery while still providing an efficient actuation of an ossicle of the middle ear.

Now, in order to implement these and still further objects of the invention, which will become more readily apparent as the description proceeds, the implantable hearing aid for mechanically actuating an ossicle of the middle ear is manifested by the features that it comprises a transducer structure for being arranged on an external side of the temporal bone and for generating vibrations, a vibration transmitter for extending through a groove in the bony external auditory canal wall and into the middle ear and connected to said transducer structure for mechanically transmitting said vibrations from said transducer structure through the external auditory canal into the middle ear, and a connector for mechanically connecting said vibration transmitter to said ossicle.

In another aspect of the invention, the hearing aid comprises a transducer structure for being arranged on an external side of the temporal bone and for generating vibrations, a substantially rigid rod structure for extending through a groove in the bony external auditory canal wall and into the middle ear, which rod-structure is connected to said transducer structure for mechanically transmitting said vibrations from said transducer structure through the external auditory canal into the middle ear, and a connector for mechanically connecting said rod structure to said ossicle.

In a further aspect of the invention, the hearing aid comprises a transducer structure for being arranged on an external side of the temporal bone and for generating vibrations, wherein said transducer structure comprises a receiver and decoder section as well as a transducer section thinner than said receiver and decoder section and extending therefrom, a vibration transmitter for extending through a groove in the bony external auditory canal wall and into the middle ear and connected to an end of said transducer section for mechanically transmitting said vibrations from said transducer structure through the external auditory canal into the middle ear, and a connector for mechanically connecting said vibration transmitter to said ossicle.

In yet another aspect, the invention provides a method for implanting a hearing aid into an ear comprising the steps of creating a groove along the bony external auditory canal wall, inserting a vibration transmitter into said groove, mechanically connecting said vibration transmitter to an ossicle of the inner ear, implanting a transducer structure on an external side of the temporal bone, and connecting said transducer structure to said vibration transmitter.

Milling a groove along the auditory canal wall avoids the problems that occur when drilling a wide access into the temporal bone. The auditory canal is easy to access and the position of the groove can be readily controlled intraoperatively. The skin of the external auditory canal can be left intact. After implantation the skin then covers the groove with the actuator arm resting in it.

Preferably, the vibration transmitter comprises a substantially rigid rod structure, which extends through the groove in the auditory canal. For easy adaptation to anatomical conditions, it can preferably be attached under a plurality of angles to the transducer structure and/or it is adjustable in length, e.g. by being telescopically extendible. The rigid rod structure can be enclosed in a tubular sleeve for isolating its vibrations.

The vibration transmitter is preferably coupled to the incus, especially the long process of the incus. This arrangement has the advantage that push/pull motions of the vibration transmitter are substantially parallel to the natural movements of incus and stapes. Therefore, an efficient coupling is achieved.

The transducer structure arranged outside the cranium, preferably on the external surface of the temporal bone or in a recess formed therein, can comprise a receiver for wireless transmission of signals from an external part comprising microphone, amplifier, and battery located outside the user's head.

BRIEF DESCRIPTION OF THE DRAWINGS

The invention will be better understood and objects other than those set forth above will become apparent when consideration is given to the following detailed description thereof. Such description makes reference to the annexed drawings, wherein.

DETAILED DESCRIPTION OF THE INVENTION

Figure 1:
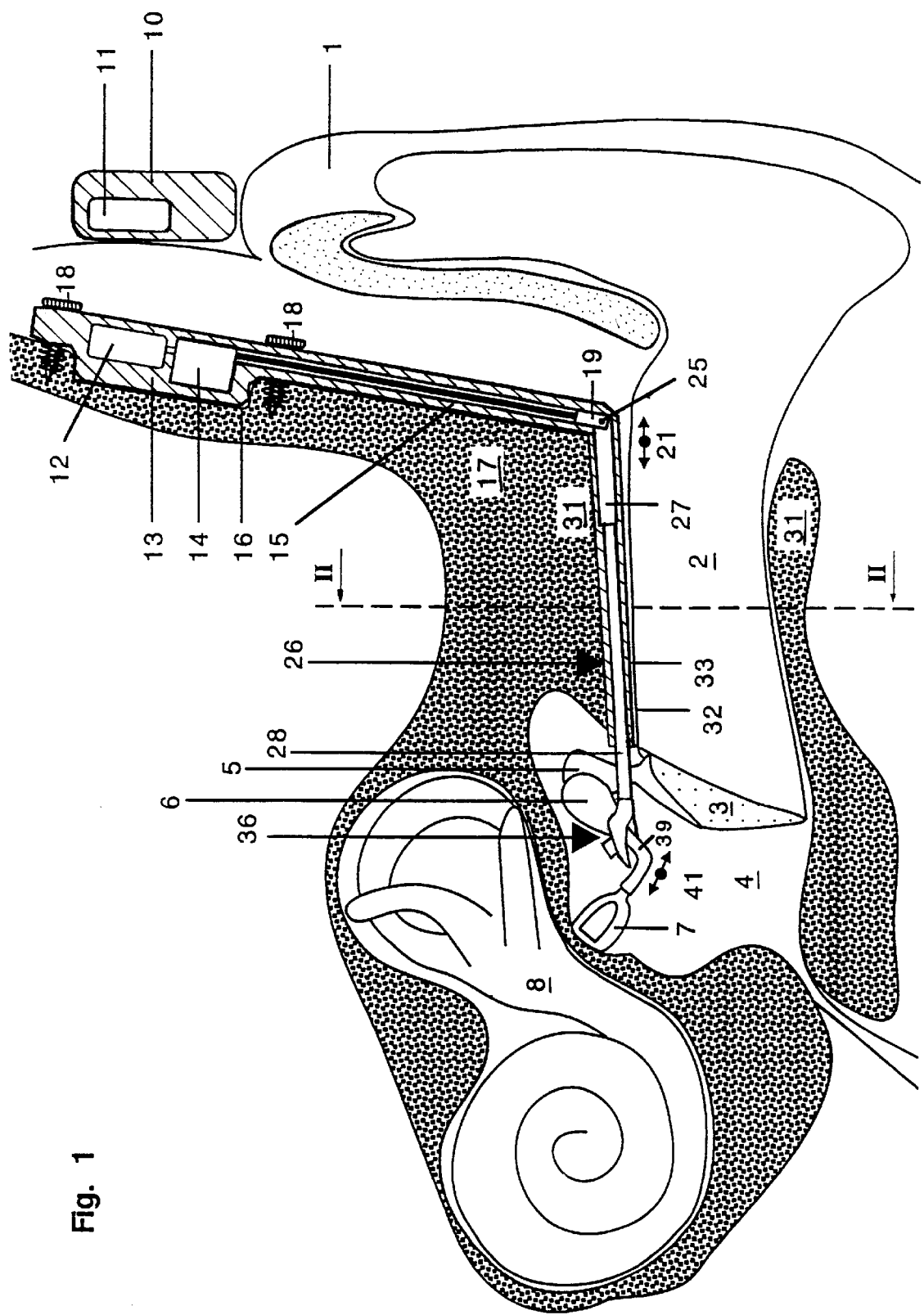
FIG. 1 a diagrammatic sectional view of a human ear in a coronal cut with an implanted hearing aid.

The basic design of a preferred embodiment of the invention is illustrated in FIG. 1. This figure depicts a section through a human ear with pinna 1, auditory canal 2, tympanic membrane 3, middle ear cleft 4 with malleus 5, incus 6 and stapes 7, and inner ear 8.

The external part 10 of this semi-implantable hearing aid comprises a microphone, amplifier, and battery, arranged behind or above the pinna 1 outside the user's head with an RF transmitter 11 to send the detected acoustic signals to a corresponding receiver 12 of the implanted hearing aid. The receiver 12 is located in a transducer structure 13, which comprises a decoder 14 and a transducer 15. Part of the transducer structure 13 is arranged in an artificial recess 16 on the outer surface of the temporal bone 17. Transducer 15 is integrally connected to decoder 14 and attached to the temporal bone 17 by means of screws 16. A piezoelectric or electromagnetic transducer 15 is arranged in the transducer arm for generating oscillations of the end 19 of transducer 15 along arrows 21.

Length and orientation of transducer structure 13 are thus that end 19 of transducer arm 15 is located at the periphery of external auditory canal 2.

An articulated joint coupling 25 connects end 19 of transducer 15 to a vibration transmitter 26, which comprises a substantially rigid rod structure with a tube 27 and a rod 28. Rod 28 is intraoperatively adjusted for appropriate length within tube 27 such that vibration transmitter 26 extends through external auditory canal 2 and into middle ear cleft 4.

As can be seen from FIG. 2, vibration transmitter 26 is cemented into a groove 30 extending along the uppermost part of the bony external auditory canal wall 31 below the intact skin 32. It is encased in a tubular sleeve 33 isolating its motions from the surrounding cement and tissue.

A clip 36 is attached to the distal end of vibration transmitter rod 28. As can be seen from FIG. 3, the clip consists of two titanium spring arms 37, which laterally enclose and hold the long processus 39 of incus 6. Clip 36 transfers the motions along arrows 21 of vibration transmitter 26 to incus 6, thereby generating motions along arrows 41. Since arrows 21 and 41 are nearly parallel, the transmittal is nearly loss-free and physiologically unnatural strain on the ossicles is avoided.

Figure 2:
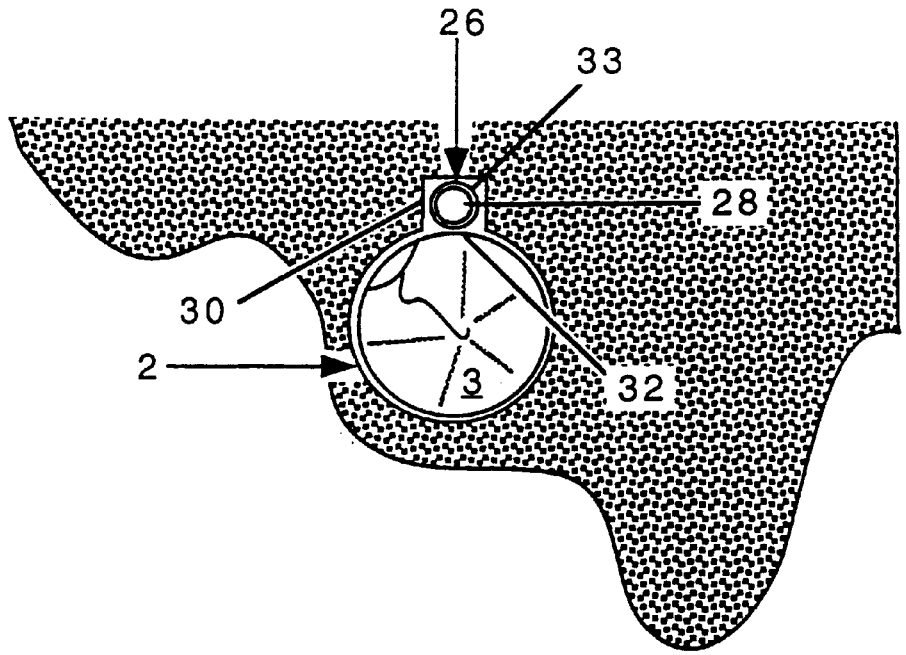
FIG. 2 a section along line II—II of FIG. 1.
Figure 3:
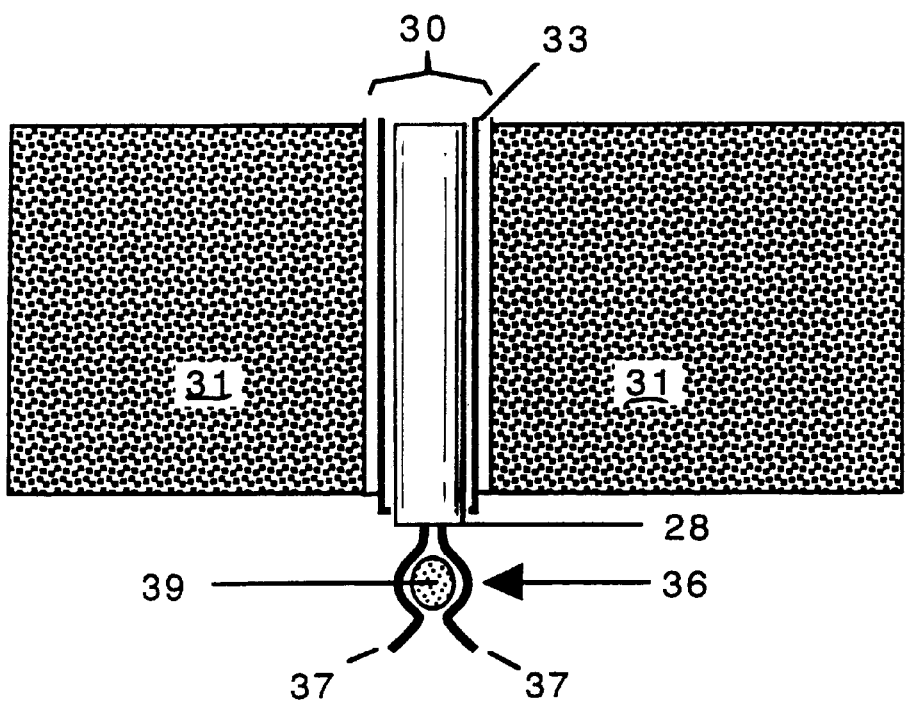
FIG. 3 a section through the long process of the incus.

The hearing aid according to FIGS. 1–3 can be implanted easily. The milling of groove 30 can be carried out accurately because of the easy access provided by auditory canal 2 after lifting off the external auditory canal skin. The angle of joint coupling 25 and the length of vibration transmitter 26 can be adjusted quickly to fit the implant into the patient's ear.

The embodiment shown in the figures is only one of the possibilities to implement a hearing aid according to the invention. Various other designs are also suited for taking advantage of a groove milled into the bony external auditory canal wall.

For example, vibration transmitter 26 can be a tube of suitable length containing a liquid and clip 36 can be affixed to an end-membrane thereof. In this case, vibrations can be transmitted through the liquid.

Instead to clip 36, glue or cement can be used for affixing vibration transmitter 26 to incus 6. Clip 36 is, however, preferred because of the ease of its application and because of the proven biocompatability of titanium in the middle ear.

While there are shown and described presently preferred embodiments of the invention, it is to be distinctly understood that the invention is not limited thereto but may be otherwise variously embodied and practiced within the scope of the following claims.

What is claimed is:

1. An implantable hearing aid for mechanically actuating an ossicle of the middle ear comprising
   a transducer structure for being arranged on an external side of the temporal bone and for generating vibrations,
   a vibration transmitter for extending through a groove in the bony external auditory canal wall and into the middle ear and connected to said transducer structure for mechanically transmitting said vibrations from said transducer structure through the external auditory canal into the middle ear, and
   a connector for mechanically connecting said vibration transmitter to said ossicle.

2. The hearing aid of claim 1, wherein said vibration transmitter comprises a substantially rigid rod structure for extending through said groove in the bony external auditory canal wall and into the middle ear.

3. The hearing aid of claim 2, wherein said rod structure is attachable under a plurality of angles to said transducer structure.

4. The hearing aid of claim 2, wherein said rod structure is adjustable in length.

5. The hearing aid of claim 4, wherein said rod structure is telescopically extendable.

6. The hearing aid of claim 2, wherein said vibration transmitter further comprises a tubular sleeve enclosing said rod structure.

7. The hearing aid of claim 1, wherein said connector comprises means for connecting said vibration transmitter to the ear's incus.

8. The hearing aid of claim 1, wherein said connector comprises means for connecting said vibration transmitter to the long process of the incus of the ear.

9. The hearing aid of claim 8, wherein said connector comprises a clip having two arms for laterally holding the long process of the incus while pushing and pulling the long process of the incus.

10. The hearing aid of claim 1, wherein said transducer structure comprises a receiver and decoder section as well as a transducer section thinner than said receiver and decoder section and extending therefrom, wherein said vibration transmitter is connected to an end of said transducer section.

11. The hearing aid of claim 1, further comprising a microphone-, amplifier- and battery assembly for arrangement outside the head and means for wireless transmission of signals from said microphone-, amplifier and battery-assembly to said transducer structure.

12. The hearing aid of claim 1, wherein said transducer structure is suited for attachment to the external surface of the temporal bone.

13. The hearing aid of claim 1, wherein said transducer structure is suited for attachment to a recess arranged on said external surface.

14. An implantable hearing aid for mechanically actuating an ossicle of the middle ear comprising
   a transducer structure for being arranged on an external side of the temporal bone and for generating vibrations,
   a substantially rigid rod structure for extending through a groove in the bony external auditory canal wall and into the middle ear, which rod-structure is connected to said transducer structure for mechanically transmitting said vibrations from said transducer structure through the external auditory canal into the middle ear, and
   a connector for mechanically connecting said rod structure to said ossicle.

15. An implantable hearing aid for mechanically actuating an ossicle of the middle ear comprising
   a transducer structure for being arranged on an external side of the temporal bone and for generating vibrations, wherein said transducer structure comprises a receiver and decoder section as well as a transducer section thinner than said receiver and decoder section and extending therefrom,
   a vibration transmitter for extending through a groove in the bony external auditory canal wall and into the middle ear and connected to an end of said transducer section for mechanically transmitting said vibrations from said transducer structure through the external auditory canal into the middle ear, and a connector for mechanically connecting said vibration transmitter to said ossicle.

16. A method for implanting a hearing aid into an ear comprising the steps of creating a groove along the bony external auditory canal wall, inserting a vibration transmitter into said groove, mechancally connecting said vibration transmitter to an ossicle of the inner ear, implanting a transducer structure on an external side of the temporal bone, and connecting said transducer structure to said vibration transmitter.

\* \* \* \* \*